United States Patent
Kamakura et al.

(10) Patent No.: US 8,563,799 B2
(45) Date of Patent: Oct. 22, 2013

(54) WOUND-COVERING HYDROGEL MATERIAL

(75) Inventors: Takashi Kamakura, Kita-gun (JP); Aki Sato, Higashikagawa (JP); Makoto Takahashi, Sapporo (JP); Takehiko Ohura, Sapporo (JP)

(73) Assignee: Teikoku Seiyaku Co., Ltd., Kagawa (JP)

(*) Notice: Subject to any disclaimer, the term of this patent is extended or adjusted under 35 U.S.C. 154(b) by 57 days.

(21) Appl. No.: 12/918,626

(22) PCT Filed: Feb. 25, 2008

(86) PCT No.: PCT/JP2008/053193
§ 371 (c)(1),
(2), (4) Date: Aug. 20, 2010

(87) PCT Pub. No.: WO2009/107189
PCT Pub. Date: Sep. 3, 2009

(65) Prior Publication Data
US 2010/0324464 A1 Dec. 23, 2010

(51) Int. Cl.
*A61F 13/00* (2006.01)
(52) U.S. Cl.
USPC .............................. 602/43; 602/42; 424/443
(58) Field of Classification Search
USPC ................. 602/43, 45, 42, 41; 442/118, 119
See application file for complete search history.

(56) References Cited

U.S. PATENT DOCUMENTS

| | | |
|---|---|---|
| 4,415,628 A | 11/1983 | Cioca et al. |
| 5,160,328 A | 11/1992 | Cartmell et al. |
| 5,693,624 A | 12/1997 | Hardy et al. |
| 5,846,214 A | 12/1998 | Makuuchi et al. |
| 6,262,330 B1 * | 7/2001 | Fujisawa et al. ............... 602/54 |
| 2003/0165560 A1 | 9/2003 | Otsuka et al. |
| 2004/0166183 A1 * | 8/2004 | Ruseler-van Embden et al. ............... 424/773 |
| 2009/0221947 A1 | 9/2009 | Uematsu |

FOREIGN PATENT DOCUMENTS

| | | |
|---|---|---|
| EP | 1 967 170 A1 | 9/2008 |
| JP | 4-272765 | 9/1992 |
| JP | 2000175959 | * 12/1998 |
| JP | 2000-175959 | 6/2000 |
| JP | 2003-225298 | 8/2003 |
| JP | 2006-61263 | 3/2006 |

(Continued)

OTHER PUBLICATIONS

New Zealand Examination Report issued Mar. 1, 2011 in corresponding New Zealand Application No. NZ 587365.
English language abstract of JP 2008-073287 published Apr. 3, 2008.
English language abstract of JP 2000-175959 published Jun. 27, 2000.

(Continued)

*Primary Examiner* — Victoria J Hicks
(74) *Attorney, Agent, or Firm* — Wenderoth, Lind & Ponack, L.L.P.

(57) ABSTRACT

A wound-covering hydrogel material which has excellent stretchability and absorbs exudates from wounds. It can maintain over long a wet environment which is suitable for accelerating the healing of wounds. There is no fear of causing pain or damaging the regenerated skin when the wound-covering hydrogel material is replaced with a fresh one. The wound-covering hydrogel material prepared by spreading a hydrogel comprising a water-soluble semi-synthetic polymer, glycerol and water, on a laminated two-layer film composed of a polyurethane film and hydrophobic fibers. The covering material has a moisture permeability as measured by the cup method in accordance with JIS Z0208 of 500-2,000 $(g/m^2/24\ h)$.

4 Claims, 1 Drawing Sheet

(56) References Cited

FOREIGN PATENT DOCUMENTS

| | | |
|---|---|---|
| JP | 2007-217387 | 8/2007 |
| JP | 2008-73287 | 4/2008 |
| NZ | 243404 | 7/1992 |
| WO | 02/22182 | 3/2002 |
| WO | 2007/077639 | 7/2007 |

OTHER PUBLICATIONS

International Preliminary Report on Patentability with English translation of Written Opinion issued Oct. 14, 2010 in corresponding International (PCT) Application No. PCT/JP2008/053193.

International Search Report issued May 1, 2008 in International (PCT) Application No. PCT/JP2008/053193.

* cited by examiner

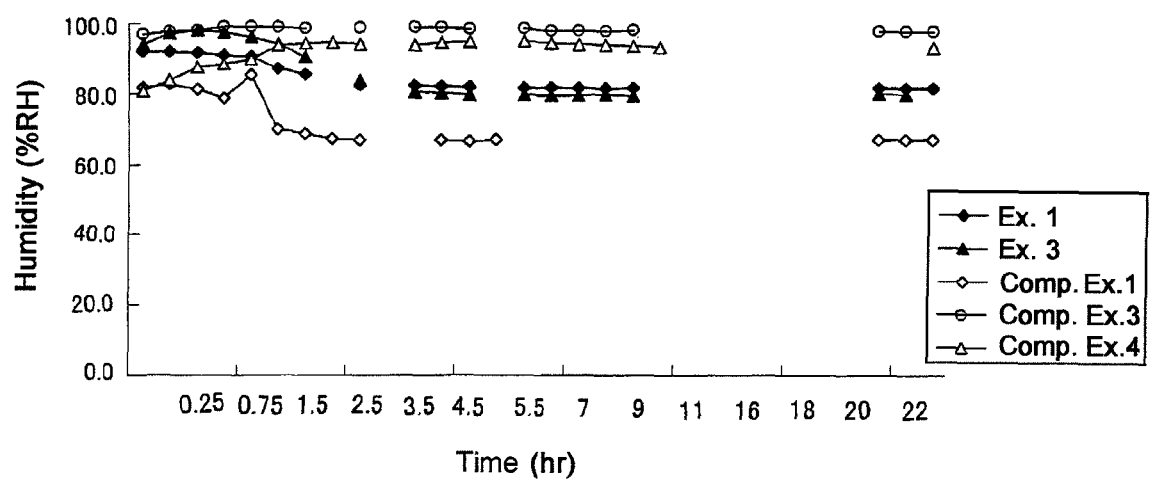

WOUND-COVERING HYDROGEL MATERIAL

This application is a national stage entry of PCT/JP2008/053193 filed Feb. 25, 2008.

TECHNICAL FIELD

The present invention relates to a wound-covering hydrogel material which is excellent in stretchability and absorbs exudate from wound surface, can maintain a moist environment suited for promoting the healing of a wound surface for many hours, and will hardly cause pain or give a damage to the regenerated skin in case of replacement of the wound-covering material with a flesh one.

BACKGROUND ART

Gauzes, powders, sprays, ointments, creams, sponges and the like have so far been used as therapeutic dressings for a wound surface. Most of them serve to absorb exudates from a wound surface to thereby dry the wound area and promote the healing thereof. In recent years, however, it has been revealed that a wound healing promoting effect can be produced by allowing the exudate to remain on the wound surface to thereby maintain the wound area in an appropriately moist environment rather than by drying the wound area; the necessity of maintaining the wound area in an appropriately moist environment has thus been recognized, and certain wound-covering materials suited therefor have been developed.

The conditions required of a wound-covering material include, among others, absorbency, moisture-maintaining ability, bacterial invasion preventing ability, bacterial growth inhibiting ability, mechanical strength, adhesiveness, and transparency. The term "mechanical strength" means that the wound-covering material will not be disintegrated even after absorption of exudate and will not leave fragments thereof on the wound area on the occasion of replacement. Transparency is required so that the affected site may be observed by the eye.

The known wound-covering materials include polyurethane films, hydrocolloids, PVA hydrogels, and alginate gels, among others.

Among the wound-covering materials mentioned above, wound-covering materials prepared by spreading an acrylic adhesive on a polyurethane film are excellent in stretchability, but have no absorbency of exudate at all; therefore, when applied to the exuding wound surface, they allow fluid accumulation to occur, whereupon drainage becomes necessary. Furthermore, they have strong tackiness, so that they may cause pain and/or damage the regenerated skin on the occasion of replacement (cf. Patent Documents 1, 2 and 3).

Hydrocolloids absorb exudates as a result of swelling of hydrophilic colloid particles contained in a hydrophobic base and, therefore, they are excellent in absorbency; however, they tend to leave gel-like substance residues on the wound surface on the occasion of replacement. Further, many of them are semi-transparent or nontransparent, making them difficult to observe the wound surface. Furthermore, they are strong in tackiness, so that they may cause pain and/or damage the regenerated skin on the occasion of replacement.

PVA hydrogels contain about 80% of purified water in each preparation and, therefore, they are really excellent in maintaining moist environments, in alleviation of pain due to cooling effect and in transparency; however, they have little tackiness, so that fixation members such as bandages or surgical tapes are required. A proposal has been made to subject PVA hydrogels to such a treatment as exposure to radiation so that they may acquire tackiness (cf. Patent Document 4); however, the tackiness is still unsatisfactory.

Alginate gels are excellent in hemostatic effect and absorbency of exudate; since, however, the gelation is caused by exudates, a gel-like substance tends to remain on the wound surface on the occasion of replacement; moreover, since they build up open systems, it becomes necessary to cover them with a film material for the purpose of moisture maintenance, bacterial invasion prevention and bacterial growth inhibition (cf. Patent Document 5).

Therefore, a wound covering hydrogel material has been desired for which is excellent in stretchability and absorbs exudate, can maintain a moist environment suited for promoting the healing of the wound surface for a prolonged period of time and hardly causes pain or give a damage to the regenerated skin on the occasion of replacement of the wound-covering material with a new one.

Patent Document 1: Japanese Patent Publication A 58-87153
Patent Document 2: Japanese Patent Publication A 4-272765
Patent Document 3: Japanese Patent Publication A 2006-61263
Patent Document 4: Japanese Patent No. 3773983
Patent Document 5: Japanese Patent Publication A 8-187280

DISCLOSURE OF INVENTION

Problem to be Solved by Invention

Accordingly, it is an object of the present invention to provide a wound covering hydrogel material which is excellent in stretchability and absorbs exudate from wound surface, can maintain a moist environment suited for promoting the healing of the wound surface for a prolonged period of time and hardly causes pain or give a damage to the regenerated skin on the occasion of replacement of the wound-covering material with a new one.

Means for Solving the Problem

As a result of intensive investigations made by the present inventors to obtain such a wound-covering material as mentioned above, it was found that a wound-covering hydrogel material which is excellent in stretchability and in protecting a wound surface, absorbs exudate, can maintain a moist environment suited for promoting the healing of the wound surface for a prolonged period of time and hardly causes pain or gives a damage to the regenerated skin on the occasion of replacement of the wound-covering material with a new one can be obtained by spreading a hydrogel containing a water-soluble synthetic or semi-synthetic polymer, glycerol and water on a laminated two-layer film composed of a polyurethane film and a hydrophobic fiber layer so that the covering material may have a moisture permeability of 500-2,000 ($g/m^2/24$ h) as measured by the cup method in accordance with JIS Z 0208. As such the present invention was completed.

Effects of Invention

The wound-covering hydrogel material according to the present invention has the following effects, among others: it is excellent in stretchability and in protecting a wound surface, absorbs exudate, can maintain a moist environment suited for promoting the healing of the wound surface for a long period of time and raises no fear of causing pain or damaging the regenerated skin on the occasion of replacement of the wound-covering material with a new one.

Thus, the present invention relates to a wound-covering hydrogel material which is prepared by spreading a hydrogel containing a water-soluble synthetic or semi-synthetic polymer, glycerol and water, on a laminated two-layer film composed of a polyurethane film and hydrophobic fibers, and said wound-covering hydrogel material having a moisture permeability of 500-2,000 ($g/m^2/24$ h) as measured by the cup method in accordance with JIS Z 0208.

Further, when the support used includes a polyurethane film having a thickness of 5-25 μm and a percentage elongation under constant load of 5% or higher, a degree of transparency which makes it possible to observe the wound surface can be secured while the wound surface can be maintained in an appropriate moist environment. Furthermore, when a moisture permeability of the laminated two-layer film composed of a polyurethane film and hydrophobic fibers is adjusted within the range of 200-5,000 ($g/m^2/24$ h) as measured by the calcium chloride method in accordance with JIS L 1099, such effects as long-term maintenance of an appropriate moist environment and prevention of skin irritation due to sweatiness can also be obtained.

When the water content in the hydrogel is 30-80%, the wound-covering material can have an appropriate level of tackiness. Thus, the material can have both the effect of maintaining an appropriately moist environment on the wound surface and the effect of preventing skin damaging due to peeling on the occasion of wound-covering material replacement. In addition, the material is advantageous in that it can secure a high level of absorbency of exudate.

BRIEF DESCRIPTION OF DRAWING

FIG. 1 The FIGURE shows the courses of changes in local humidity with time in respective wound-covering materials.

BEST MODE FOR CARRYING OUT THE INVENTION

In the following, the present invention is explained in more detail.

The wound-covering hydrogel material according to the present invention has a moisture permeability of 500-2,000 ($g/m^2/24$ h), preferably 700-1,500 ($g/m^2/24$ h), as measured by the cup method in accordance with JIS Z 0208. At moisture permeability levels lower than 500 ($g/m^2/24$ h), skin irritation due to sweatiness may unfavorably be encountered. Levels higher than 2,000 ($g/m^2/24$ h) are also unfavorable since, at such levels, the wound surface can no longer be maintained in an appropriate moist environment over a prolonged period of time.

The polyurethane resin constituting the polyurethane film in the practice of the present invention is not particularly restricted but may be a common urethane resin, for example of the ether or ester type.

The polyurethane film to be used in the practice of the present invention preferably has a thickness of 5-25 μm and a percentage elongation under constant load of 5% or higher. Polyurethane film thicknesses less than 5 μm are unfavorable since the mechanical strength is insufficient and the increase in number of pinholes results in failure to maintain the wound surface in an appropriately moist environment. On the contrary, when the thickness is in excess of 25 μm, the percentage elongation under constant load becomes less than 5% and the stretchability is thus impaired; hence it becomes difficult to protect the wound surface. The transparency also decreases and, unfavorably, it becomes impossible to observe the wound surface.

Usable as the hydrophobic fibers to be laminated on the polyurethane film are polyester, nylon, acrylic, polypropylene and polyethylene fibers, among others.

The laminated two-layer film composed of a polyurethane film and hydrophobic fibers thus produced preferably has a moisture permeability within the range of 200-5,000 ($g/m^2/24$h), more preferably 300-3,000 ($g/m^2/24$ h), as measured by the calcium chloride method in accordance with JIS L 1099 so that a moist environment suited for promoting the healing of the wound surface may be maintained for a prolonged period of time. At moisture permeability levels higher than 5,000 ($g/m^2/24$ h), a moist environment cannot be kept for a long period, hence the effect of promoting the healing of the wound surface will become lower. Levels lower than 200 ($g/m^2/24$ h) are unfavorable since, at such levels, skin irritation due to sweatiness may possibly occur.

As the water-soluble synthetic or semi-synthetic polymer to be used in the practice of the present invention, there may be mentioned, for example, polyacrylic acid, sodium polyacrylate, partially neutralized polyacrylate, polyacrylic acid starch, hydroxypropylcellulose, hydroxypropylmethylcellulose, hydroxyethylcellulose, methylcellulose, carmellose sodium, carboxyvinyl polymers and N-vinylacetamide copolymers; these can be used singly or in combination of two or more species. In particular, combinations of two or more of carboxyvinyl polymers, polyacrylic acid, partially neutralized polyacrylate and carmellose sodium are preferred.

The proportion of the water-soluble synthetic or semi-synthetic polymer in the hydrogel is preferably 3-20% by weight, more preferably 5-15% by weight. When that proportion is smaller than 3% by weight, the gel viscosity will be too low, making it difficult to mold the gel into patches, whereas proportions in excess of 20% by weight are unfavorable since the water-soluble synthetic or semisynthetic polymer will no longer be dissolved uniformly in the gel, thus failing to form a good gel.

The content of water in the hydrogel is preferably 30-80% by weight, more preferably 40-75% by weight, relative to the gel weight. The water content in excess of 80% by weight is unfavorable, since the absorbency of exudate will decrease. Water content levels below 30% by weight are unfavorable, since the tackiness becomes excessively strong, so that there arises the possibility of causing pain or damaging the regenerated skin on the occasion of wound-covering material replacement or the failure to maintain a moist environment suited for promoting the healing of the wound surface as a result of a decrease in skin moisture-retaining effect.

The content of glycerol in the hydrogel is preferably 10-40% by weight, more preferably 15-30% by weight. When the glycerol content in the hydrogel is lower than 10% by weight, the skin moisture-retaining effect decreases and it is no longer possible to maintain a moist environment suited for promoting the healing of the wound surface. When the glycerol content in the hydrogel is higher than 40% by weight, a portion of glycerol which cannot be retained floats to the gel surface, causing such problems as stickiness on the occasion of application and decreases in tackiness.

The hydrogel-constituting component or components other than those mentioned above are not particularly restricted provided that they will not lessen the effects of the present invention; thus, for example, one or more of fillers, humectants, stabilizers, and crosslinking agents may be incorporated in the hydrogel.

Usable as the fillers are, for example, kaolin, titanium dioxide, silicic anhydride, zinc oxide, and bentonite, either singly or in combination of two or more species. Since, however, it is necessary for the hydrogel to have transparency so that the wound surface may be observed after application of the hydrogel to the wound surface, silicic anhydride is particularly preferred and the level of addition thereof is preferably 0.1-5% by weight.

Usable as the humectants other than glycerol are, for example, D-sorbitol solutions, 1,3-butylene glycol, dipropylene glycol, polyethylene glycol, polypropylene glycol and sodium DL-pyrrolidonecarboxylate solutions, either singly or in combination of two or more species, and the level of addition thereof is preferably 10-30% by weight.

From the viewpoint of the skin irritability, the hydrogel preferably has a pH within the range of 3.5-6.5, more preferably within the range of 4.0-5.5. Tartaric acid, sodium hydrogensulfite, edetic acid salts and the like are used as pH-adjusting agents.

Usable as the crosslinking agents are, for example, dried aluminum hydroxide gel, aluminum glycinate, dihydroxyaluminum aminoacetate, synthetic hydrotalcite, metal salt aluminometasilicates and other polyvalent metal compounds, either singly or in combination of two or more species. The level of addition thereof may vary depending on the species employed but is preferably 0.001-1% by weight.

If necessary, one or more of preservatives, antioxidants, plasticizers, emulsifiers, surfactants and the like may further be incorporated in the hydrogel.

The wound-covering hydrogel material of the present invention, when applied to a wound area, is required to have such a level of tackiness as to allow the material to move on with the movements of the skin and, on the occasion of replacement, is required to show such a level of tackiness at which the regenerated skin will not be damaged. Therefore, the wound-covering hydrogel material of the present invention has a tackiness of 8-12 as expressed in terms of ball number at the time of application (before absorption of water), and the ball number at the time of replacement (after 8-hour water absorption) should be not higher than 3. If the ball number at the time of application is 8-12, the material, when applied to the wound area, can have an appropriate level of tackiness so as to enable the same to move on with the skin movements. If the ball number is less than 8, the initial tackiness is insufficient and the covering material, when applied to a movable wound area, cannot move on with the skin movements, thus unfavorably causing the problem of peeling off soon. If the ball number is in excess of 12, the covering material, when applied to the wound area, is too strong in tackiness and may unfavorably cause skin irritation. On the other hand, when the ball number at the time of replacement is 3 or smaller, the corresponding tackiness is such a level at which no pain is caused or the regenerated skin will never be damaged, whereas, when the ball number is in excess of 3, the tackiness is excessively high, which is unfavorable since there arises the possibility of causing pain or damaging the regenerated skin on the occasion of replacement.

Each ball number value referred to above means the value obtained by carrying out the ball tack test according to the ball tack test method prescribed in JIS Z 0237 at an inclination angle of 30°.

Usable as the plastic film for covering the hydrogel surface are polyethylene films, polypropylene films, polyester films and polyvinyl chloride films, or films obtained by subjecting these films to such surface treatment as silicone treatment, corona discharge treatment, roughening treatment or plasma treatment.

The wound-covering hydrogel material of the present invention can be manufactured by any of those methods known in the art. For example, the wound-covering hydrogel material can be manufactured by spreading a hydrogel constituted according to such a composition as described above on a support and covering the hydrogel surface with a plastic film.

The covering material can be subjected to such an ordinary sterilization treatment as radiation sterilization, electron beam sterilization or ethylene oxide sterilization according to need.

EXAMPLES

The following examples and comparative examples illustrate the present invention more specifically. These examples are, however, by no means limitative of the scope of the present invention.

Example 1

A carboxyvinyl polymer (1.6 g) was dissolved in an appropriate amount of purified water, and D-sorbitol solution (20 g) was then added to the solution, followed by stirring until the mixture became homogeneous. The mixture was further uniformly mixed with polyacrylic acid (0.3 g), tartaric acid (1.2 g), concentrated glycerol (20.7 g), carmellose sodium (3.5 g), partially neutralized polyacrylate (4 g), silicic anhydride (0.1 g), castor oil (1.5 g), dihydroxyaluminum aminoacetate (0.07 g), sodium edetate (0.08 g) and purified water (appropriate amount) to prepare a hydrogel. This hydrogel was spread on a urethane (20 μm)/nylon elastomer (25 g/m$^2$) laminate and the gel surface was covered with a polyester film to produce a wound-covering hydrogel material.

Example 2

A wound-covering hydrogel material was manufactured by preparing a hydrogel in the same manner as in Example 1 using the components for Example 2 as specified in Table 1 and spreading the hydrogel on a urethane (20 μm)/nylon tricot laminate (support) and covering the hydrogel surface with a polyester film.

Example 3

Silicic anhydride (0.5 g) was dissolved in an appropriate amount of purified water, and urea (1.0 g), sodium edetate (0.08 g) and castor oil (0.5 g) were added, followed by stirring until the mixture became uniform. The mixture was further mixed uniformly with a 20% aqueous solution of poly(acrylic acid) (15.0 g), tartaric acid (0.3 g), concentrated glycerol (16.0 g), carmellose sodium (4.0 g), partially neutralized poly(acrylic acid) (5.0 g), magnesium aluminometasilicate (0.06 g), dried aluminum hydroxide gel (0.02 g) and an appropriate amount of purified water to prepare a hydrogel. This hydrogel was spread on a urethane (20 μm)/nylon elastomer (25 g/m$^2$) laminate and the gel surface was covered with a polyester film to produce a wound-covering hydrogel material.

Comparative Example 1

A covering material was manufactured by preparing a hydrogel in the same manner as in Example 1 using the components for Comparative Example 1 as specified in Table 1 and spreading the hydrogel on a nonwoven PET fabric (100 g/m$^2$).

Comparative Example 2

A covering material was manufactured by preparing a hydrogel in the same manner as in Example 1 using the components for Comparative Example 2 as specified in Table 1 and spreading the hydrogel on a PET (20 μm)/nonwoven PET fabric (35 g/m$^2$) laminate.

TABLE 1

| Component (wt %) | Ex. 1 | Ex. 2 | Ex. 3 | Comp Ex. 1 | Comp. Ex. 2 |
|---|---|---|---|---|---|
| Silicic anhydride | 0.1 | 0.1 | 0.5 | 0.1 | 0.1 |
| Polyacrylic acid | 0.3 | 0.3 | — | 0.3 | 0.3 |
| Carboxyvinyl polymer | 1.6 | 1.6 | — | 1.6 | 1.6 |
| D-sorbitol solution | 20 | 20 | — | 20 | 20 |
| Concentrated glycerol | 20.7 | 20.7 | 16 | 20.7 | 20.7 |
| Carmellose sodium | 3.5 | 3.5 | 4 | 3.5 | 3.5 |
| Partially neutralized polyacrylate | 4 | 4 | 5 | 4 | 4 |
| Castor oil | 1.5 | 1.5 | 0.5 | 1.5 | 1.5 |
| Polyacrylic acid aqueous solution (20%) | — | — | 15 | — | — |
| Tartaric acid | 1 | 1 | 0.3 | 1 | 1 |
| Urea | — | — | 1.0 | — | — |
| Dihydroxyaluminum aminoacetate | 0.07 | 0.07 | — | 0.07 | 0.07 |
| Magnesium aluminometasilicate | — | — | 0.06 | — | — |
| Dried aluminum hydroxide gel | — | — | 0.02 | — | — |
| Sodium edetate | 0.08 | 0.08 | 0.08 | 0.08 | 0.08 |
| Purified water | Adequate amount | Adequate amount | Adequate amount | Adequate amount | Adequate amount |
| Support | Urethane 20 μm/ nylon elastomer 25 g/m$^2$ | Urethane 20 μm/ nylon tricot | Urethane 20 μm/ nylon elastomer 25 g/m$^2$ | Nonwoven PET fabric 100 g/m$^2$ | PET 2 μm/ nonwoven PET fabric 35 g/m$^2$ |

Comparative Example 3

DuoACTIVE® (outer layer: polyurethane film; tacky layer: hydrophilic colloid and hydrophobic polymer particles; release paper: silicone release paper)

Comparative Example 4

OPSITE (trademark) (polyurethane film and an acrylic adhesive applied thereto)

Comparative Example 5

VIEWGEL® (support: polyethylene; hydrogel absorbent: povidone, PVA, phenoxyethanol, water (80%))

Test Example 1

The wound-covering materials of Examples 1-3 and the wound-covering materials of Comparative Example 1-5 were measured for stretchability, moisture permeability, water absorbency and tackiness by the test methods mentioned below. Each measured value is the mean of three measurements. The results obtained are shown in Table 2.

Stretchability Test

The stretchability test was carried out in accordance with "stretch fabrics" in test methods for general woven fabrics of JIS L 1096. Each test material was cut to a size of 2×6 cm and each specimen was marked at intervals of 4 cm ($L_0$). Each specimen was clipped on the outside of each mark line and placed under a constant load of 100 g, and the distance between the marks was measured ($L_1$). The stretchability was calculated as follows:

$$\text{Stretchability (\%)} = (L_0 - L_1)/L_0 \times 100$$

where $L_0$: original mark-to-mark length (4 cm);
$L_1$: mark-to-mark length (cm) under a constant load of 100 g.

Moisture Permeability Test

The moisture permeability test was carried out by the cup method in accordance with JIS Z 0208. About 10 mL of purified water was placed in a glass vessel (inside diameter: 56 mm; depth: 11 mm), the glass vessel opening was covered with a circular piece (test specimen) with a diameter of 80 mm as cut from a test material, with the hydrogel or adhesive surface facing inward, the glass vessel brim portion was sealed with a paraffin-based stretchable film, and the whole assemblage was weighed ($W_0$). The assemblage was allowed to stand in a thermo-hygrostat set at from 40° C. to 75% for 24 hours and then allowed to cool, the weight thereof was measured correctly ($W_1$), and the moisture permeability was calculated as follows:

$$\text{Moisture permeability } (g/m^2 \cdot 24\ h) = (W_0 - W_1) \times 10000 \div A$$

where $W_0$: weight (g) before test;

$W_1$: weight (g) after test;

A: glass vessel opening area (26.4 cm$^2$).

Water Absorbency Test

About 10 mL of physiological saline was placed in a stainless steel vessel (inside diameter: 88 mm, depth 15 mm), a 4×4 cm piece (test specimen) cut from a test material was placed therein, with the hydrogel or adhesive surface facing inward, and stored in the vessel in a state sealed therein for 8 hours. The test specimen weight ($W_0$) before placement in the vessel and the weight ($W_1$) of the test specimen taken out after the lapse of 8 hours were compared.

Amount of water absorbed: $W_1 - W_0$

Tackiness Test

A test apparatus as described in Drug Approval and Licensing Procedures in Japan 2005 (Part IV: Applications for Drug Approval and Licensing, Chapter 1: Tackiness test) was used, and a test preparation was placed on an inclined plane forming an angle of 30 degrees with a horizontal, with the tacky surface of the preparation facing upward. An upper 10-cm-long portion and a lower 15-cm-long portion were covered respectively with appropriate sheets of paper to leave a 5-cm-long middle portion of the tacky surface. A series of steel balls varying in diameter from 3.2 mm to 34.9 mm were allowed to roll down from the upper end of the inclined plane, and the number of balls which stopped on the middle tacky surface for at least 5 seconds was determined. Test preparations before water absorption and test preparations after 8 hours of water absorption were evaluated in this manner.

TABLE 2

|  |  | Ex. 1 | Ex. 2 | Ex. 3 |
|---|---|---|---|---|
| Stretchability (%) | Lengthwise | 14.2 | 5.0 | 50 |
|  | Widthwise | 15.0 | 39.2 | 55 |
| Moisture permeability (g/m$^2$/24 h) |  | 884 | 1385 | 1367 |
| Water absorption (g/8 h/16 cm$^2$) |  | 2.52 | 2.79 | 2.71 |
| Tackiness (ball number) | Before water absorption | 10 | 10 | 11 |
|  | After water absorption | 2 | 2 | 3 |

|  |  | Comp. Ex. 1 | Comp. Ex. 2 | Comp. Ex. 3 | Comp. Ex. 4 | Comp. Ex. 5 |
|---|---|---|---|---|---|---|
| Stretchability (%) | Lengthwise | 12.5 | 0 | 5.7 | 12.5 | 2.5 |
|  | Widthwise | 23.3 | 0 | 5.8 | 10.8 | 2.5 |
| Moisture permeability (g/m$^2$/24 h) |  | 1935 | 661 | 343 | 377 | 28 |
| Water absorption (g/8 h/16 cm$^2$) |  | 2.02 | 2.37 | 0.64 | 0 | 1.14 |
| Tackiness (ball number) | Before water absorption | 8 | 7 | 21 | 17 | 3 |

TABLE 2-continued

|  |  |  |  |  |  |
|---|---|---|---|---|---|
| After water absorption | 3 | 1 | 2 | 8 | 1 |

Test Example 2

The support respectively used in the wound-covering materials of Examples 1-3 and the wound-covering materials of Comparative Examples 1-2 were subjected to moisture permeability test by the calcium chloride method (method A-1; 40° C.-90% RH) as prescribed in JIS L 1099: Test methods for water vapor permeability of textiles. The results obtained are shown in Table 3.

TABLE 3

|  | Ex. 1 | Ex. 2 | Ex. 3 | Comp. Ex. 1 | Comp. Ex. 2 |
|---|---|---|---|---|---|
| Moisture permeability (g/m$^2$/24 h) | 1282 | 3699 | 3799 | 8541 | 942 |

Test Example 3

Each of the wound-covering materials of Examples 1-3 and the wound-covering materials of Comparative Examples 1, 3 and 4 was applied onto a moistened sponge. The sponge was placed in a stainless steel vessel with warm water at 37° C. circulating therein. Further, a temperature/humidity sensor was inserted between the wound-covering material and the sponge, and the changes in application site temperature and humidity were temporally measured for 24 hours. The results are shown in FIG. 1.

Discussion

As regards the wound-covering materials of Comparative Examples 3 and 4 (moisture permeabilities of the preparations: 343 and 377, respectively), which are commercial products, FIG. 1 indicates that the application site humidity arrived at nearly 100% after about 2 hours from the application and this condition lasted for 24 hours. This fact suggests that when either of the wound-covering materials of Comparative Examples 3 and 4 is applied to the surface of a wound, exudate from the wound surface tends to be retained on the wound surface because of the excessively low moisture permeability of the preparation, with the result that the wound surface may be maintained in an excessively moist condition; thus, in the case of long-time application, sweatiness and/or disagreeable sensation may possibly be caused at the application site, raising problems, for example making it necessary to frequently replace the wound-covering material. Regarding the wound-covering material of Comparative Example 1, the humidity at the application site began to decrease immediately after application and, after 2 hours from the application, the humidity was about 60%, and this condition continued for 24 hours. This fact suggests that when the wound-covering material of Comparative Example 1 in which a support high in moisture permeability (moisture permeability of the support: 8541) is used is applied to a wound area, the moisture on the wound surface will begin to be lost immediately after application, leading to failure to maintain a proper moist environment and, in the case of long-time application, the hydrogel will be dehydrated, possibly allowing the adhesion between the regenerated skin and the hydrogel to occur and thus intensifying the fear of the regenerated skin being damaged on the occasion of replacement.

On the contrary, as for the wound-covering materials of Examples 1 and 3 according to the present invention (moisture permeabilities of the preparations: 884 and 1367, respectively), it is shown that the humidity begins to decrease slowly immediately after application but a humidity of about 80% is retained over 24 hours, hence a moist condition favorable for wound healing can be maintained for a prolonged period of time.

Thus, it can be seen from the results obtained in this test example that when the wound-covering materials according to the present invention with a support having a moisture permeability of 200-5,000 (g/m$^2$/24 h) is applied onto a wound area, the hydrogel absorbs the exudate on the wound surface and the exudate is inhibited from being retained thereon as a result of permeation, through the support, of surplus water in exudate, so that the wound surface does not become in an excessively moist state, but a moist environment suited for promoting the healing of the wound surface can be maintained for a prolonged period of time; namely, it was revealed that the covering materials maintain a moist environment suited for promoting the healing of the wound surface.

Test Example 4

The wound-covering materials of Examples 1-3 and the wound-covering materials of Comparative Examples 3-5 which are commercially available were evaluated for skin adhesion and for pain at the time of peeling off by applying each of them to the forearm of each of five volunteers for 4 hours in accordance with following criteria.

Skin Adhesion

Skin adhesion evaluations were made on the three-rank system: "no peeling off", "half peeling off" and "peeling off". The results obtained are shown in Table 4.

TABLE 4

| | Ex. 1 | Ex. 2 | Ex. 3 | Comp. Ex. 3 | Comp. Ex. 4 | Comp. Ex. 5 |
|---|---|---|---|---|---|---|
| Score | 1 | 1 | 2 | 1 | 1 | 3 |

Evaluation criteria/scores:
1: no peeling off;
2: half peeling off;
3: peeling off Pain on the Occasion of Peeling Off Evaluations for pain on the occasion of peeling off from a skin were made on the three-rank system: "not painful at all", "little painful" and "painful"; the results are shown in Table 5.

TABLE 5

| | Ex. 1 | Ex. 2 | Ex. 3 | Comp. Ex. 3 | Comp. Ex. 4 | Comp. Ex. 5 |
|---|---|---|---|---|---|---|
| Score | 1 | 1 | 1 | 3 | 3 | 1 |

Evaluation criteria/scores:
1: not painful at all;
2: little painful;
3: painful

The invention claimed is:

1. A wound-covering hydrogel material which is prepared by spreading a hydrogel comprising 5-15% by weight of a water-soluble synthetic or semi-synthetic polymer selected from combinations of two or more of carboxyvinyl polymers, polyacrylic acid, partially neutralized polyacrylate and carmellose sodium, 15-30% by weight of glycerol, 40-75% by weight of water and 0.001-1% by weight of one or more crosslinking agents selected from the group consisting of dried aluminum hydroxide gel, aluminum glycinate, dihydroxyaluminum aminoacetate, synthetic hydrotalcite, and metal salt aluminometasilicates on a laminated two-layer film composed of a polyurethane film and hydrophobic fibers;
   wherein the wound-covering hydrogel material has a moisture permeability of 500-2,000 (g/m$^2$/24 h) as measured by a cup method in accordance with JIS Z 0208; and the wound-covering hydrogel material has a tackiness of 8-12 as expressed in terms of ball number before absorption of water and a tackiness of not higher than 3 as expressed in terms of ball number after 8-hours of water absorption.

2. The wound-covering hydrogel material according to claim 1, wherein the polyurethane film has a thickness of 5 to 25 µm and a percentage elongation under constant load of 5% or higher.

3. The wound-covering hydrogel material according to claim 2, wherein the laminated two-layer film composed of a polyurethane film and hydrophobic fibers has a moisture permeability of 200-5,000 (g/m$^2$/24 h) as measured by a calcium chloride method in accordance with JIS L 1099.

4. The wound-covering hydrogel material according to claim 1, wherein the laminated two-layer film composed of a polyurethane film and hydrophobic fibers has a moisture permeability of 200-5,000 (g/m$^2$/24 h) as measured by a calcium chloride method in accordance with JIS L 1099.

* * * * *